United States Patent
Kuo et al.

(10) Patent No.: US 7,279,135 B2
(45) Date of Patent: Oct. 9, 2007

(54) PROBE FOR PROVIDING MICRO LIQUID DROPS

(75) Inventors: Chia-Lung Kuo, 6 F, No. 207, Lane 125, Sec. 3, Dasyue Road, Douliou City, Yunlin County (TW); Jr Shiang You, Taipei (TW); Yu Long Huang, Tanzih Township, Taichung County (TW); Ching-Yi Wu, No. 43, Guancian Road, Baoshan Township, Hsinchu County (TW)

(73) Assignees: Taiwan Micro System Co., Ltd., Taipei County (TW); Chia-Lung Kuo, Yunlin County (TW); Ching-Yi Wu, Hsinchu County (TW)

( * ) Notice: Subject to any disclaimer, the term of this patent is extended or adjusted under 35 U.S.C. 154(b) by 645 days.

(21) Appl. No.: 10/841,532

(22) Filed: May 10, 2004

(65) Prior Publication Data

US 2005/0269371 A1    Dec. 8, 2005

(51) Int. Cl.
*B05C 1/00* (2006.01)
*B05C 19/06* (2006.01)

(52) U.S. Cl. .............. 422/100; 222/420; 222/421; 222/436; 73/863.43; 73/864.51

(58) Field of Classification Search ............... 422/100, 422/64, 63, 67, 68.1; 73/863.22, 152.23; 222/420, 484, 35.7; 401/258, 221; 436/180, 436/174; 178/18.01
See application file for complete search history.

(56) References Cited

U.S. PATENT DOCUMENTS

| | | | | | |
|---|---|---|---|---|---|
| 223,618 | A | * | 1/1880 | MacKinnon | 118/500 |
| 911,336 | A | * | 2/1909 | Schweizer | 401/221 |
| 1,112,362 | A | * | 9/1914 | Matsumoto | 401/227 |
| 1,379,602 | A | * | 5/1921 | Abegg | 401/258 |
| 3,306,267 | A | * | 2/1967 | Matsumoto | 401/258 |
| 4,971,763 | A | * | 11/1990 | Columbus | 422/100 |
| 6,497,155 | B1 | * | 12/2002 | Feygin et al. | 73/863.22 |

* cited by examiner

*Primary Examiner*—Walter D. Griffin
*Assistant Examiner*—Christine T Mui
(74) *Attorney, Agent, or Firm*—Rosenberg, Klein & Lee

(57) ABSTRACT

A probe for providing micro liquid drops including a main rod, a limiting portion and a probe tip portion is disclosed. At least one guiding flow way and several storing recesses are disposed on the conical outer surface of the probe tip portion. Each storing recess has a volume that is larger than the volume of the guiding flow way. Also, under the gravity and capillarity effect, the output speed is controlled by the number, size and shape of the guiding flow ways and the storing recesses so that each probe structure is strong, the liquid storing capacity is high, its liquid output is stable, it is easier to manufacture the guiding flow ways, and it is easy to clean.

6 Claims, 9 Drawing Sheets

PROBE FOR PROVIDING MICRO LIQUID DROPS

BACKGROUND OF INVENTION

1. Field of the Invention

The present invention relates to a probe for providing micro liquid drops. Particularly, it can form a probe array for providing micro liquid drops, especially for sample or reagent dispensing in which, the structure of each probe is strong, the liquid storing capacity is high, its liquid output is stable, it is easier to manufacture the guiding flow ways, and it is easy to clean.

2. Description of the Prior Art

Referring to FIGS. 10 and 11, it shows a conventional probe structure 90 on a laboratory carrier tray 80. This conventional probe structure 90 has an upper end and a lower end. It further comprises:

a limiting head 91 disposed on the upper end of the probe structure 90 for hanging on the laboratory carrier tray 80;

a probe body 92 extending from the limiting head 92 toward the lower end of the probe structure 90 so that the probe body 92 can be moved on the laboratory carrier tray 80; and a liquid providing end 93 formed at the lower end of on the probe structure 90 and connecting with the probe body 92. This liquid providing end 93 has a liquid releasing port 931 at the lower end of the probe structure 90. The liquid providing end 93 has an axial open channel 932 and a storage portion 933. The axial open channel 932 has a width W. The function of the storage portion 933 is to store a working fluid 70 (not shown) therein.

However, the disadvantages of the conventional probe structure 90 can be listed as follows:

[1] The structure of the liquid providing end is weak. In order to release the working fluid 70, the liquid providing end 93 has to hit another object (such as a laboratory sample array carrier or the like). Because the liquid providing end 93 is split into two parts, its structure is weaker, especially at the hitting moment where it might influence the width W (getting wider or deforming). As a result, the volume of the out liquid each time will be slightly altered and becomes unstable.

[2] The liquid storing capacity is limited. The volume of storing portion 933 of the conventional probe structure 90 is relatively small, so its liquid storing capacity is limited. If the stored liquid is not sufficient, the user has to re-fill several times during an experiment or testing. Thus, it will cause unnecessary interruption and delay.

[3] The output liquid is unstable. The volume of each output droplet is gradually reduced meaning that the output liquid is unstable. At the beginning, the droplet is larger, but at the end, the droplet becomes smaller and will decrease the accuracy of the experiment or the testing. In addition, if just increasing the width of the axial open channel 932 too much, the capillarity effect will be reduced and the output droplet cannot remain constant.

[4] The surface of the axial open channel is too rough and the channel's size cannot be too small. The axial open channel 932 usually is manufactured by wire cut electrical discharging machining, so the surface of the axial open channel 932 is rough. However, due to the wire's tensile strength and melting point limitation, the diameter of the wire cannot be too small. In addition, there are two discharging gaps on both sides of the wire, so the minimum width of the axial open channel 932 cannot be too narrow. Thus, the rough surface and the channel's size will influence the flowing condition.

[5] It is hard to clean due to the liquid's viscosity and the narrow space of the open channel 932 and the storage portion 933, the liquid is easy to stick inside. Such liquid residue needs to be completely washed out. In fact, it's hard to clean.

SUMMARY OF THE INVENTION

The primary object of the present invention is to provide a probe for providing micro liquid drops that has a strong probe structure and can afford the contacting force while it is hitting on the surface of an object.

The second object of the present invention is to provide a probe for providing micro liquid drops that has a larger liquid storing capacity.

The other object of the present invention is to provide a probe for providing micro liquid drops, in which the liquid output is stable by utilizing the unique design of the guiding flow ways and several storing recesses.

The next object of the present invention is to provide a probe for providing micro liquid drops that can be made by existing plastic injection method so as to enhance the profile accuracy and reduce the cost.

Another object of the present invention is to provide a probe for providing micro liquid drops that is easy to clean.

DETAILED DESCRIPTION OF THE PREFERRED EMBODIMENT

Figure 1:
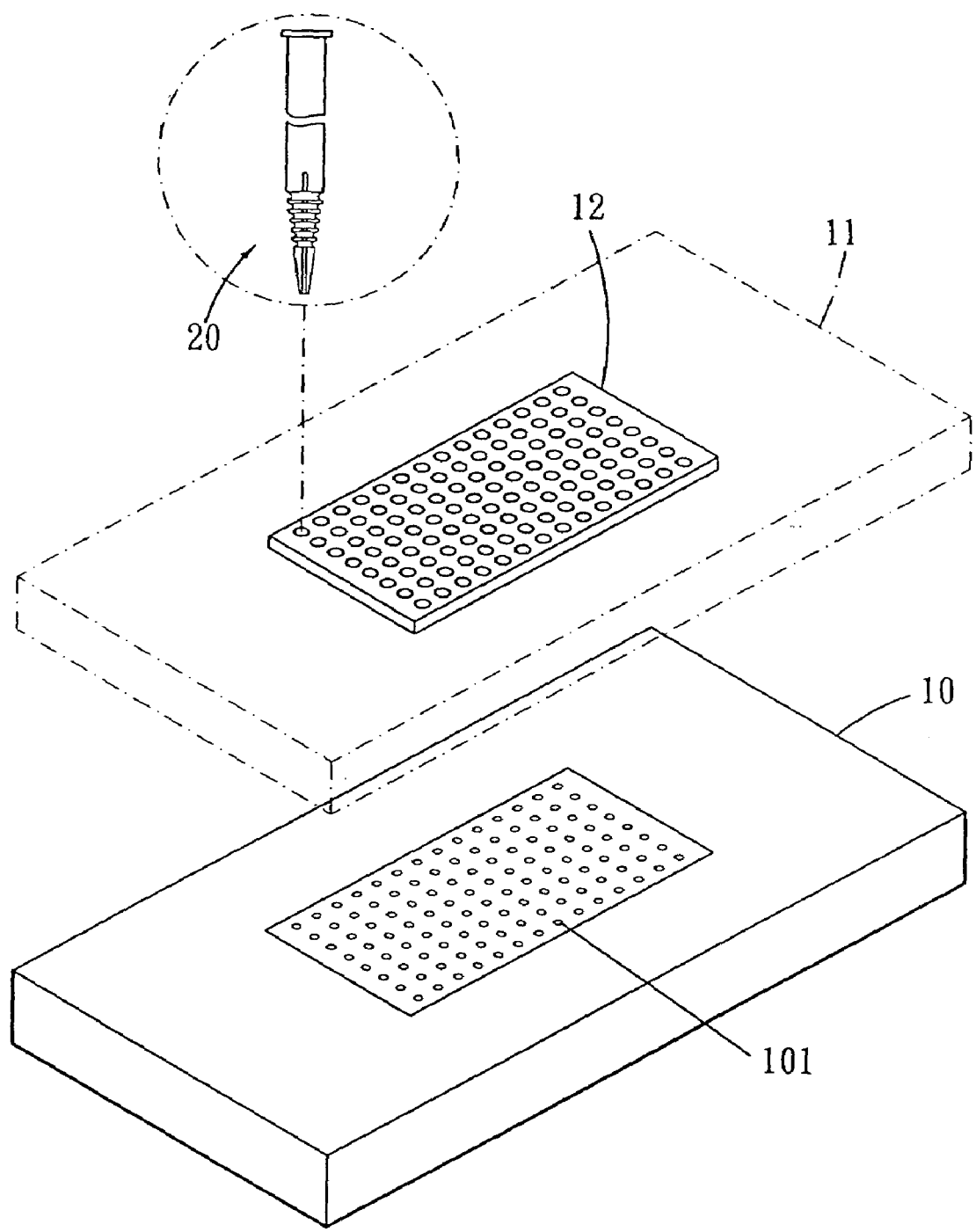
FIG. 1 illustrates the present invention used in a testing equipment.
Figure 2:
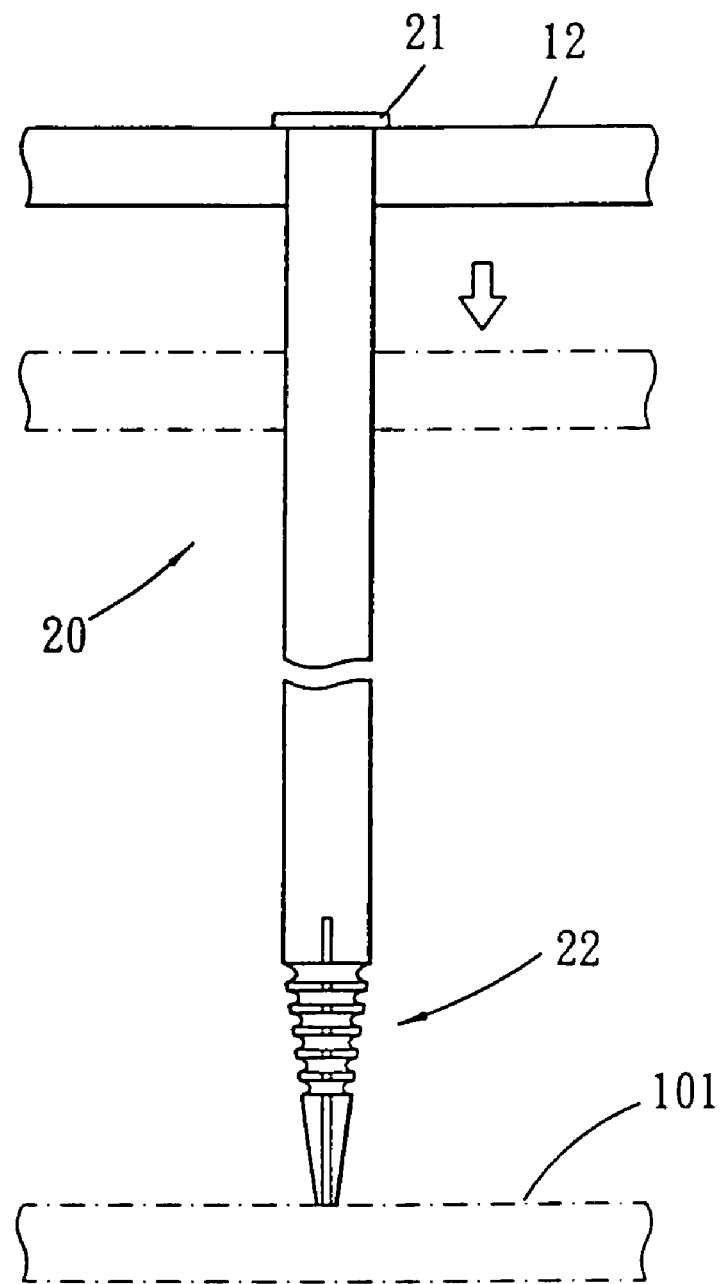
FIG. 2 is a front view of the present invention.
Figure 3:
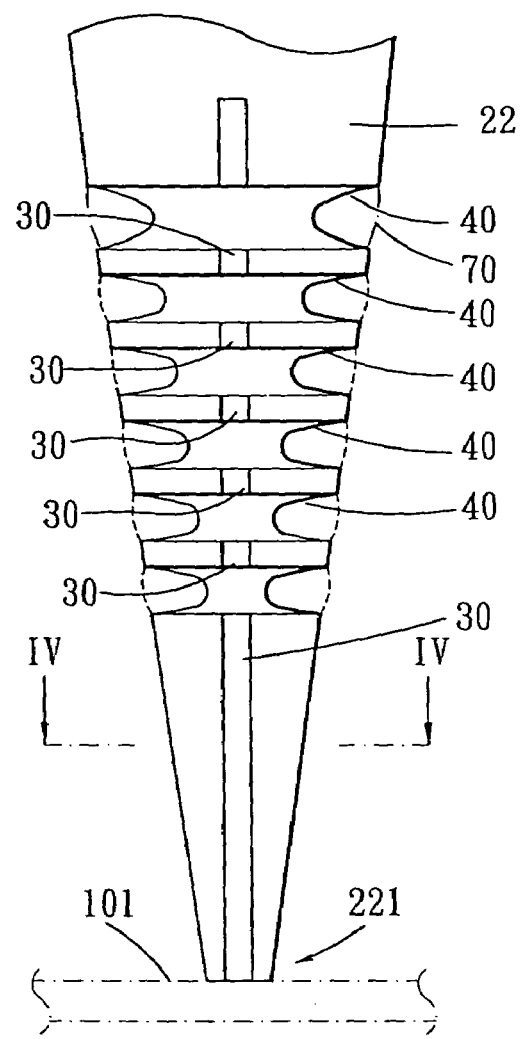
FIG. 3 is an enlarged view of a selected portion of the present invention.
Figure 4:
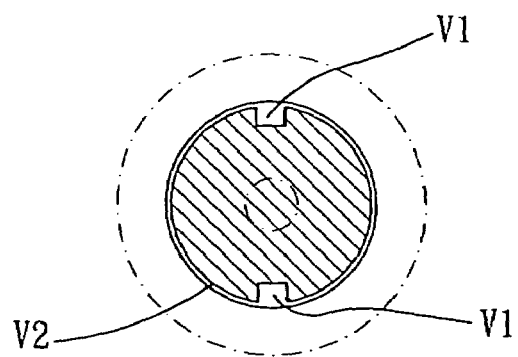
FIG. 4 is a cross-sectional view of the present invention.
Figure 5:
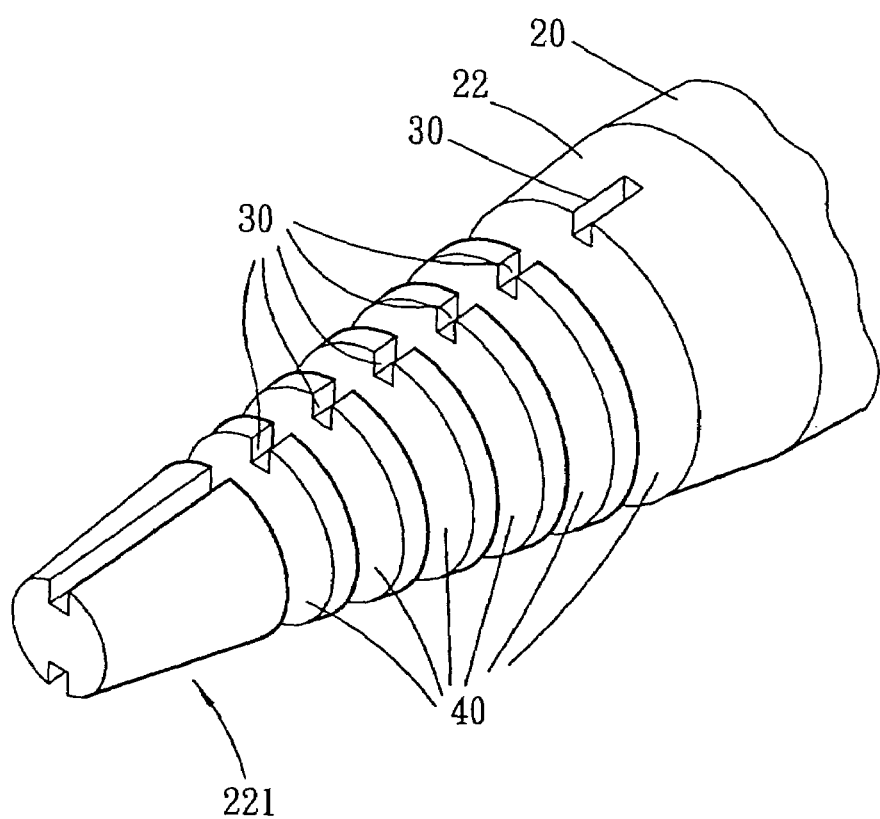
FIG. 5 is a perspective view of a selected portion of the present invention.

Referring to FIGS. 1 to 2, for most mass sample analysis, usually a sampling plate 10 having a plurality of testing droplets 101 (such as an array) is used. There is a hanging frame 11 disposed with a probe tray 12 for allowing many probes (such as a probe array) vertically hanging on.

As shown in FIGS. 1 to 4, the present invention relates to a probe for providing micro liquid drops mainly comprises a main rod 20, a limiting portion 21 and a probe tip portion 22.

The main rod 20 has an upper end and a lower end.

The limiting portion 21 is disposed on the upper end of the main rod 20.

The probe tip portion 22 is disposed on the lower end of the main rod 20. The probe tip portion 22 has a substantially conical outer surface and a contacting end 221. A diameter of the contacting end 221 is less than 0.5 mm. The conical outer surface further has:

(a) a plurality of guiding flow ways 30 extending from the contacting end 221 and substantially evenly-distributed on the conical outer surface; and the guiding flow ways 30 having a first volume V1; and (b) a plurality of storing recesses 40; each of the storing recess 40 being around the conical outer surface with a predetermined depth and a given cross-sectional shape; the storing recesses 40 being able to communicate with the guiding flow ways 30; the storing recesses 40 having a second volume V2 that is larger than said first volume V1;

so that the main rod 20 can store and provide micro liquid (such as a working fluid 70).

More specifically about this embodiment, the main rod 20 is substantially solid cylindrical and there are two guiding flow ways 30 that are axially disposed and approximately equally spaced.

In addition, the limiting portion 21 of the main rod 20 hangs on a hole of a probe tray 12 having a plurality of holes (see FIG. 1). The main rods 20 can move up or down within a range.

About the actual operation of the present invention, it can be described as follows:

When a user starts a mass sample analysis, the probe tray 12 of the sampling frame 10 holds a lot of probes. Then, these probes are dipped with a working fluid.

Once the contacting end 221 of the main rod 20 of the present invention contacts with the working fluid 70, the working fluid 70 will move to the guiding flow ways 30 and the storing recesses 40 by capillarity effect.

After the working fluid 70 fills the space of the guiding flow ways 30 and the storing recesses 40, the sampling plate 10 will be moved to relocate these main rods 20 at a desired location. Then, the probe tray 12 will be lowered until the contacting ends 221 of the main rods 20 contact with another object. Because it is a hanging design, the main rods 20 will automatically adjust their final vertical positions.

At this moment, due to the gravity, the working fluid 70 will flow down certain volume (see FIG. 6) on the object. For each main rod 20, a predetermined volume of the working fluid 70 will contact with the object (or testing specimen) to conduct a chemical, medical or biochemical analysis.

Figure 6:
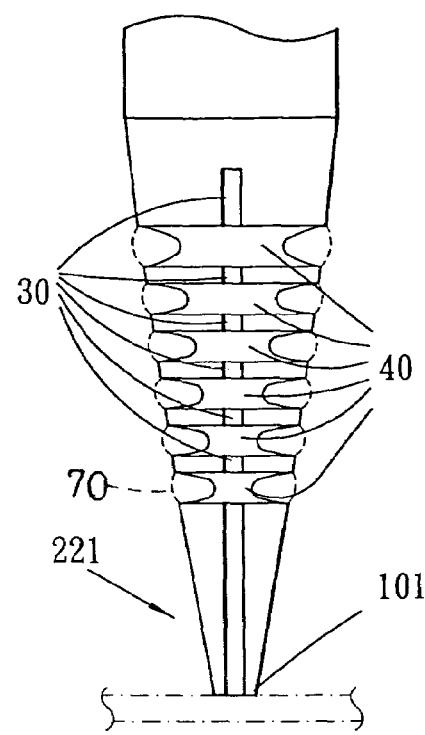
FIG. 6 shows this invention that is ready to output.
Figure 7:
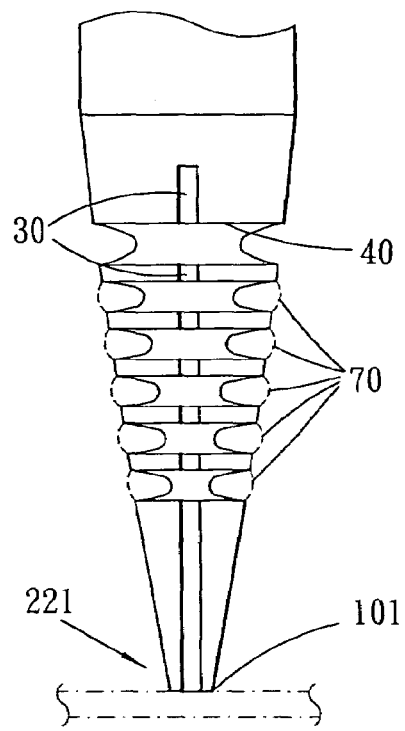
FIG. 7 shows this invention just outputs a little liquid.
Figure 8:
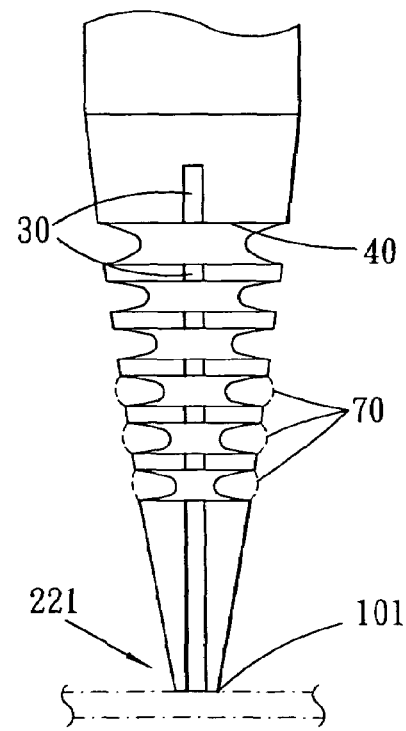
FIG. 8 shows this invention outputs more liquid.

Of course, when the contacting ends 221 are repeated to contact the testing specimens (could be different set of testing specimens), the working fluid 70 will flow down accordingly. As shown in FIGS. 6 to 8, the working fluid 70 stored in the storing recessed 40 will be gradually reduced from top to down (due to gravity).

Moreover, the storing recesses 40 are horizontal, parallel and disposed on the circular conical surface. The stored volume of storing recesses 40 is defined as the second volume V2. The second volume V2 is larger than the first volume V1 of the guiding flow ways 30. In fact, under the gravity and capillarity effect, the output speed is controlled by the number, size and shape of the guiding flow ways 30. Therefore, the output volume of the present invention is almost kept constant.

Figure 9:
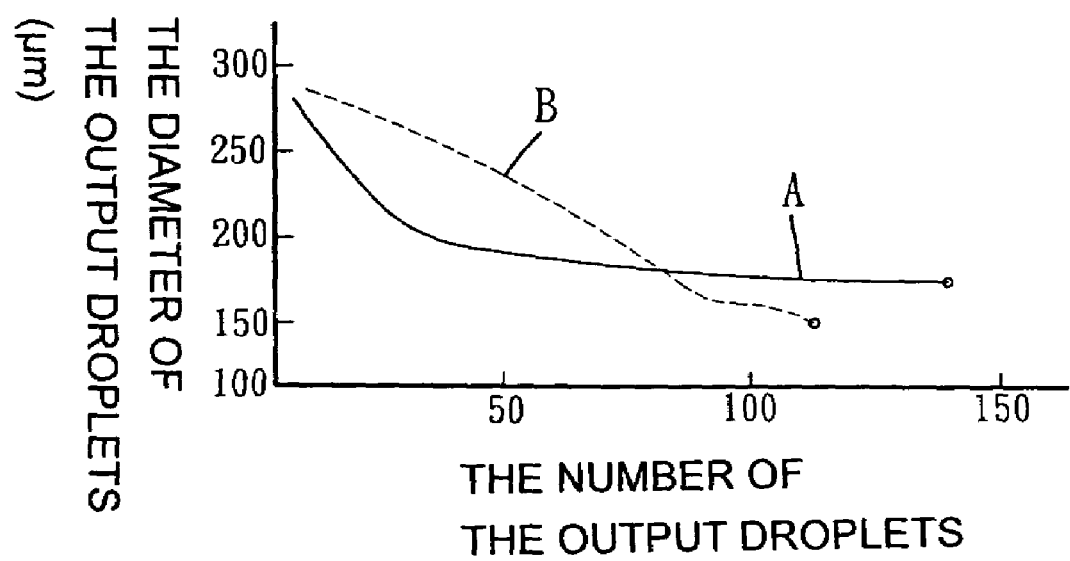
FIG. 9 illustrates the testing results of the present invention and the conventional one.
Figure 10:
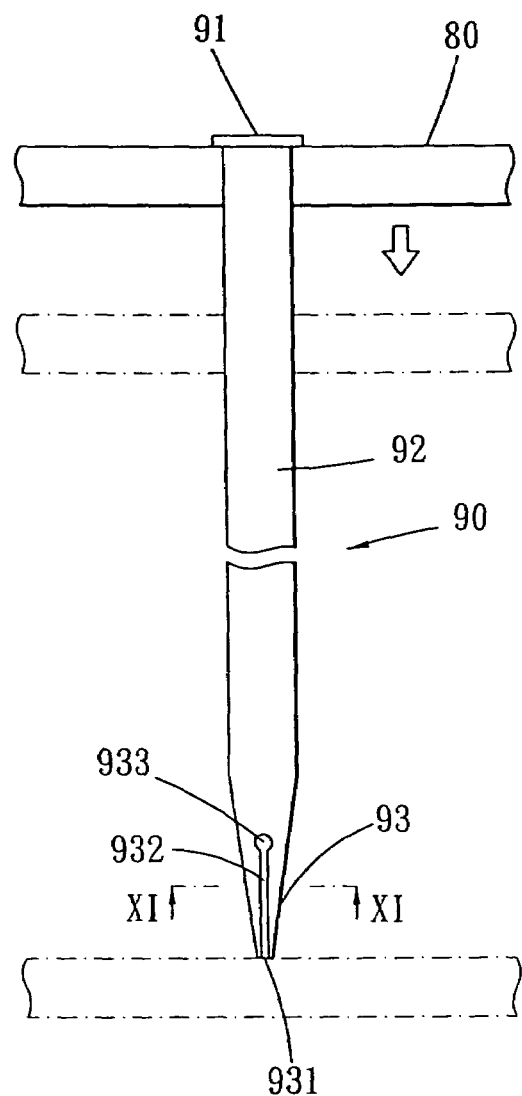
FIG. 10 is a front view of the conventional structure.
Figure 11:
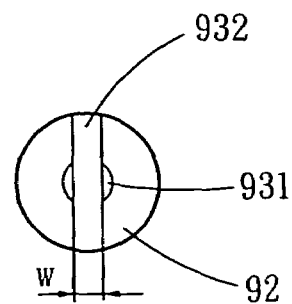
FIG. 11 is a bottom view of the conventional structure.

Referring to FIG. 9, the X-axis means the number of the output droplets ranging from 0 to 150. Also, the Y-axis means the size (or diameter) of the droplets ranging from 100 μm to 300 μm. The result of present invention is indicated by solid line A. That is, the present invention provides the droplets having a more stable output about its volume and it lasts longer (almost 150 drops). Particularly, during the 50th to the 100th droplets, they are kept approximately at 180 μm horizontally (stable output).

With regard to the conventional output characteristics, the output volume is always decreasing as shown in dotted line B. The output volume varies too much, thus the testing result of the conventional one is less reliable due to such unstably output.

In addition, the present invention can be made by plastic injection method so that the cost can be significantly reduced and the manufacturing speed can be increased.

Figure 12:
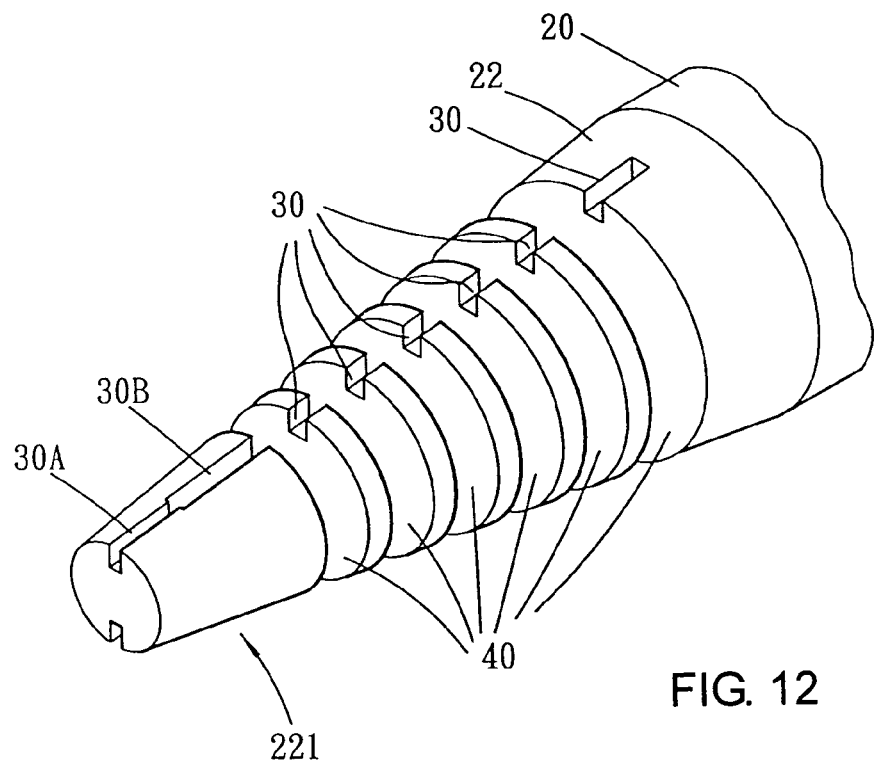
FIG. 12 shows the second embodiment of the present invention.

Referring to FIG. 12, it shows the second embodiment of the present invention. In which, each of the guiding flow ways 30 is consisted of a first channel 30A and a second channel 30B. The first channel 30A is narrower than the second channel 30B so that the working fluid 70 flowing out from the contacting end 221 can be more effectively controlled.

Figure 13:
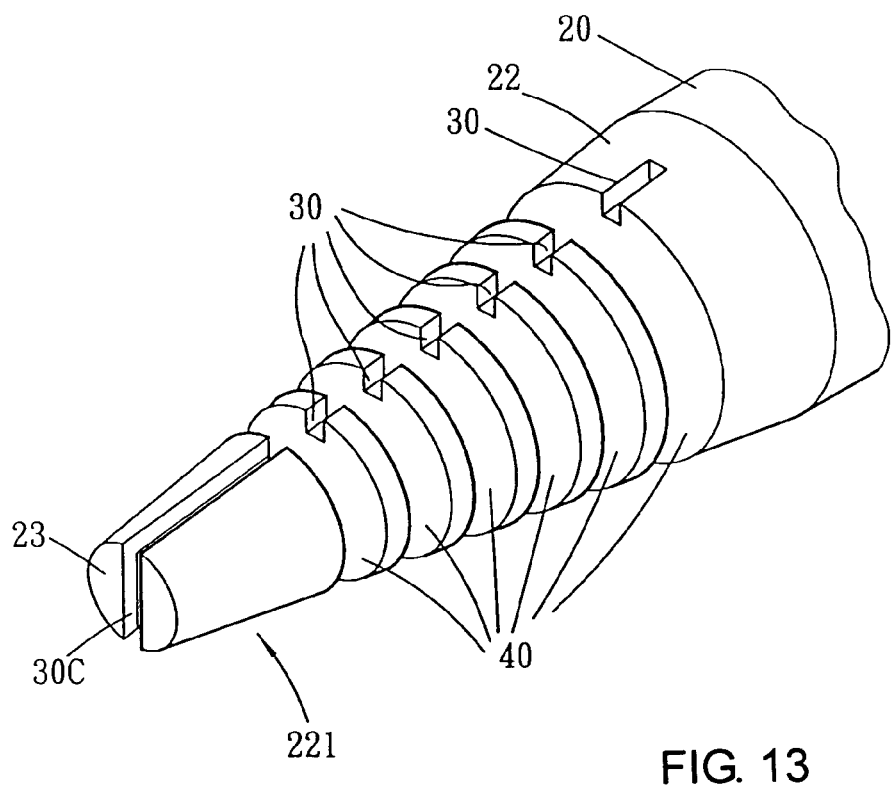
FIG. 13 shows the third channel of the present invention.

As illustrated in FIG. 13, a third channel 30C connecting with the guiding flow ways 30 is formed on a flat surface 23 of the contacting end 221.

Figure 14:
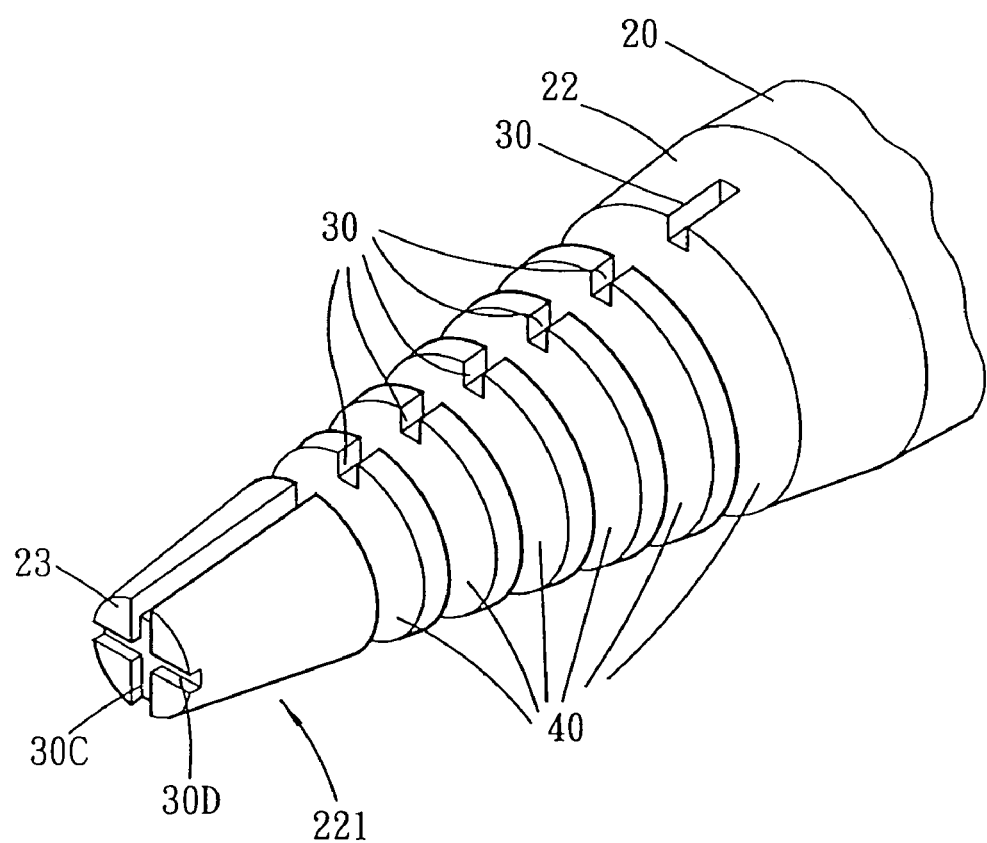
FIG. 14 shows the fourth channel of the present invention.

Or, as shown in FIG. 14, a fourth channel 30D is additionally formed on the flat surface 23 of the contacting end 221. The fourth channel 30D and the third channel 30C form a combined cross channel, thus the flowing output will be more stable and smoother.

The advantages and functions of the present invention can be summarized as follows:

[1] The structure of contacting end of the probe is strong. In this invention, the guiding flow ways and the storing recesses are formed on the outer surface of the probe tip portion. The depth is relative small, so it will not influence the structure of the probe.

[2] It has a larger liquid storage capacity. The storing recesses are formed on the conical outer surface. Its liquid storage capacity is larger than the one of the guiding flow ways. If increasing the number of the storing recesses, the total storage capacity can be raised.

[3] Its liquid output is stable. In this invention, the working fluid is stored in the storing recesses by capillarity. Once the contacting end contacts with an object or a testing specimen, the stored working fluid will flow out a certain amount. Moreover, the output flowing rate is limit by the guiding flow ways as well as the design of several storing recesses. So, in this invention, the output liquid (or droplet) will be kept substantially constant and quite stable.

[4] It is easier to manufacture the guiding flow ways. Unlike the traditional one that has to be manufactured by expensive wire cut technology, the guiding flow ways of the present invention can be easily made by the existing cheaper micro plastic injection method.

[5] It is easy to clean. The working fluid is stored in the shallow guiding flow ways and the storing recesses so it is easy to clean or wash.

The above embodiments are only used to illustrate the present invention, not intended to limit the scope thereof. Many modifications of the above embodiments can be made without departing from the spirit of the present invention.

What is claimed is:

1. A probe for providing micro liquid drops comprising:
   a main rod having an upper end and a lower end;
   a limiting portion disposed on said upper end of said main rod;
   a probe tip portion disposed on said lower end of said main rod, said probe tip portion having a substantially conical outer surface and contacting end, a diameter of said contacting end being less than 0.5 mm; said conical outer surface having:

(a) a plurality of guiding flow ways extending from said contacting end and substantially evenly-distributed on said conical outer surface; said guiding flow ways having a first volume; and (b) a plurality of storing recesses; each of said storing recess being around said conical outer surface with a predetermined depth and a cross-sectional shape; said storing recesses communicating with said guiding flow ways; said storing recesses having a second volume that is larger than said first volume;

so that said main rod can store and provide micro liquid by capillarity.

2. The probe for providing micro liquid drops as defined in claim 1, wherein said main rod is substantially solid cylindrical and four guiding flow ways are axially disposed and approximately equally spaced.

3. The probe for providing micro liquid drops as defined in claim 1, wherein said limiting portion of each main rod is movably hanging on a hole of a plate having a plurality of holes.

4. The probe for providing micro liquid drops as defined in claim 1, wherein each of the guiding flow ways is consisted by a first channel and a second channel, and said first channel is narrower than the second channel so that the working fluid flowing out from the contacting end can be more effectively controlled.

5. The probe for providing micro liquid drops as defined in claim 1, wherein a third channel connecting with said guiding flow ways is formed on a flat surface of said contacting end.

6. The probe for providing micro liquid drops as defined in claim 5, wherein a fourth channel is formed on said flat surface of said contacting end and said fourth channel and said third channel form a combined cross channel.

\* \* \* \* \*